United States Patent [19]

Moake et al.

[11] Patent Number: 4,578,642
[45] Date of Patent: Mar. 25, 1986

[54] METHOD AND APPARATUS FOR MEASURING VELOCITY OF FERROMAGNETIC TUBING

[75] Inventors: Gordon L. Moake; Marvin Milewits, both of Houston, Tex.

[73] Assignee: PA Incorporated, Houston, Tex.

[21] Appl. No.: 599,227

[22] Filed: Apr. 11, 1984

[51] Int. Cl.[4] ............... E21B 47/00; G01N 27/72; G01D 3/42
[52] U.S. Cl. ................... 324/160; 324/225; 324/226; 324/174; 175/40
[58] Field of Search ............ 175/40; 324/225, 226, 324/206, 242, 173, 160; 73/151; 246/249

[56] References Cited

U.S. PATENT DOCUMENTS

| | | | |
|---|---|---|---|
| 3,197,693 | 7/1965 | Libby | 324/225 |
| 3,328,681 | 6/1967 | Wood | 324/225 |
| 3,609,530 | 9/1971 | Johnson | 324/225 |
| 3,693,075 | 9/1972 | Förster | 324/226 |
| 3,835,374 | 9/1974 | Frost | 324/225 |
| 3,916,301 | 10/1975 | Vild | 324/226 |
| 4,079,312 | 3/1978 | Osborn | 324/226 |
| 4,270,088 | 5/1981 | Weischdel | 324/242 |
| 4,292,588 | 9/1981 | Smith | 324/225 |

*Primary Examiner*—Reinhard J. Eisenzopf
*Assistant Examiner*—Jose M. Solis
*Attorney, Agent, or Firm*—Norvell & Associates

[57] ABSTRACT

A tubing trip tool for use in determining the extent of defects in tubular elements comprising a continuous string used in a subterranean oil or gas well during removal of the string from the well is disclosed. Local defects and axially extending defects, as well as the average wall thickness of the tubular elements, are measured. The position of the defects is determined by measuring the variable velocity of the tubular elements as they are removed from the well. A noncontact axial velocity detector comprises detector elements generating a first signal dependent upon an applied magnetic field and the axial velocity of the tubular elements. The first signal is compared to a signal dependent only upon the magnetic field generated in a second element. A pickup coil and Hall effect probes can be used.

22 Claims, 11 Drawing Figures fig.1 fig. 2 fig. 3 fig.4  fig.5 fig.11 fig.6 fig.7 fig.8 fig.9 fig.10

METHOD AND APPARATUS FOR MEASURING VELOCITY OF FERROMAGNETIC TUBING

BACKGROUND OF THE INVENTION

1. Field of the Invention

This invention relates to defect inspection of tubular elements comprising a generally continuous tubular string used in a subterranean oil and gas well, and more particularly to inspection of tubular elements by detecting the properties of magnetic fields induced in the tubular elements during removal from the well at variable velocities.

2. Description of the Prior Art

Continuous tubular strings formed of connectable tubular sections or elements, such as production tubing strings, strings of drill pipe and casing strings, are used in the drilling, completion and production of subterranean oil and gas wells. The tubular elements comprising such strings are subject to mechanical damage while the tubular elements are located within the well and are also subject to the action of corrosive fluids which may be contained within the tubular elements or which may be transported through the tubular string between the well surface and a downhole location. It is therefore advantageous that the individual tubular elements comprising a tubular string be inspected periodically. Commonly, tubular elements or tubular sections are inspected for defects after the tubing string is removed from the well. Conventional inspection of tubular sections normally occurs after the individual tubing sections comprising the tubing string have been disengaged. Defect inspections are conventionally performed on a section by section basis. Occasionally, inspection is performed downhole through the use of inspection calipers. These tools leave "caliper tracks" and can be affected by the contents of the tubing.

A number of techniques exist for determining the presence of a defect in a tubing section. For example, the precise location of internal and external radially extending and three dimensional defects, including slug inclusions, mechanical damage, corrosion pitting and fatigue cracks, has been determined by flux leakage techniques in which a longitudinal magnetic field is induced by one or more magnetic induction coils. Surface riding detectors are located around the tubing and the maximum signal is recorded to precisely locate the defect. Since this magnetic inspection is conducted on a section by section basis after disengagement from the tubing string, when surface dirt, scale and mud can be controlled, detectors can be placed directly on the surface of the ferromagnetic tubular section to determine the presence of defects.

The location of longitudinal defects, including internal and external seams, plug scores, eccentricity, wear due to sucker rod interference, and wireline cuts, has been detected by inducing a circumferential magnetic field in the tubing. The field is induced by a high current discharge through an insulated rod on the interior of the tubing section. Detectors rotating around the surface of the tubing locate these longitudinal defects. Again, since the inspection is conducted on a section by section basis, the insulated rod can be inserted through the interior of the tubing section for this longitudinal defect inspection technique.

Other conventional inspection systems use methods which do not require insertion of rods and probes inside the pipe. Specifically, a common way of detecting longitudinal defects magnetically is the "rotating pole" method, where the magnetic field is applied from the outside by rotating electromagnets, and detectors positioned in-between the poles scan the outside surface of the pipe.

Tubing wall thickness has been measured by measuring the radiation from a rotating radioactive source of gamma radiation transmitted through the pipe or tubing wall of a tubing section. For example, with a source rotating around the pipe, a detector may be located on the inside of the pipe to determine the degree of attenuation of gamma radiation and thus to determine the wall thickness. Again, this technique requires access to individual tubing sections after disengagement of the string. Other ways of measuring wall thickness with gamma radiation, which are backscatter, double-wall through-transmission and chord, have both the radiation detector and the source located on the outside of the pipe. Radiation methods introduce such problems as radiation licensing, record keeping, radiation safety administration, source handling complications, and fear of the unknown.

Techniques requiring surface-riding detectors, insertion of a detector or a driving means within the bore of tubular elements or requiring rotating mechanical means to obtain a complete circumferential coverage of tubing sections are unsuited for use in defect inspection and measurement of tubing sections while the string is being removed from the well. These defect inspection techniques are also unsuited to the measurement of defects in tubing sections while the sections are interconnected in the tubing string. Thus these inspection techniques are not suitable for use on a drilling, completion or workover rig at the surface of the well to measure defects in a tubing string as the string is removed from the well. In addition to the requirements that only disengaged tubing sections be individually measured, additional problems which would be encountered are the limited space available on the rig, the inability to control the longitudinal velocity of the tubing string as it is removed from the well, and the difficulty in precisely controlling the transverse location of the tubing sections comprising the tubing string. Furthermore, the use of surface detectors in a tubing trip tool for measuring defects as tubing sections, comprising a tubing string, are removed from the well is also complicated by the presence of solid deposits, such as drilling mud, and tubing mounted components, such as retrievable packers, which may be incorporated into the tubing string.

One technique for inspecting tubular elements which is adaptable to relative movement, at variable velocities, is a technique involving the use of a saturating longitudinal magnetic field and the subsequent measurement of the time integral of the electrical signal caused by the magnetic field applied to the ferromagnetic tubular member to determine the average wall thickness. Testing using this technique has been conducted for surface pipe installations in which the magnetic field and the flux detecting elements are moved relative to a continuous pipe array. Such apparatus has not, however, been employed to measure the average wall thickness of tubing sections as they are removed from an oil or gas well.

SUMMARY OF THE INVENTION

An apparatus and method for measuring the velocity of a moving ferromagnetic tubular element, such as a tubular element in a continuous string of tubing used in an oil or gas well is disclosed. A uniform magnetic field is applied to the moving element. A first signal is dependent upon the velocity of the tubular element relative to the magnetic field and upon changing magnetic leakage fields emanating from the tubular element as a result of axial changes in the magnetic properties of the tubular element. These changing properties can result from the presence of grain boundaries within the tubular element. A pickup coil with its axis disposed perpendicular to the axis of the tubular element can be employed to obtain this signal.

A second signal dependent only upon the changing magnetic leakage fields and independent of the relative velocity of the tubular element can be obtained. Hall effect probes can be employed to obtain the second signal. In the preferred embodiment of the invention, two Hall effect probes oriented in the plane of the coil at the leading and trailing edges of the coil can be used to obtain the second signal. The Hall effect probes can be incorporated into the pickup coil and the ratio of the coil signal and the Hall effect probe will be dependent only upon the velocity of the tubular elements. The velocity sensor can be transversely spaced from the tubular elements and can be incorporated into a tubing trip tool for measuring defects in the tubular elements during removal of the tubular string from a well.

DESCRIPTION OF THE PREFERRED EMBODIMENTS

Tubing Trip Tool

Figure 1:
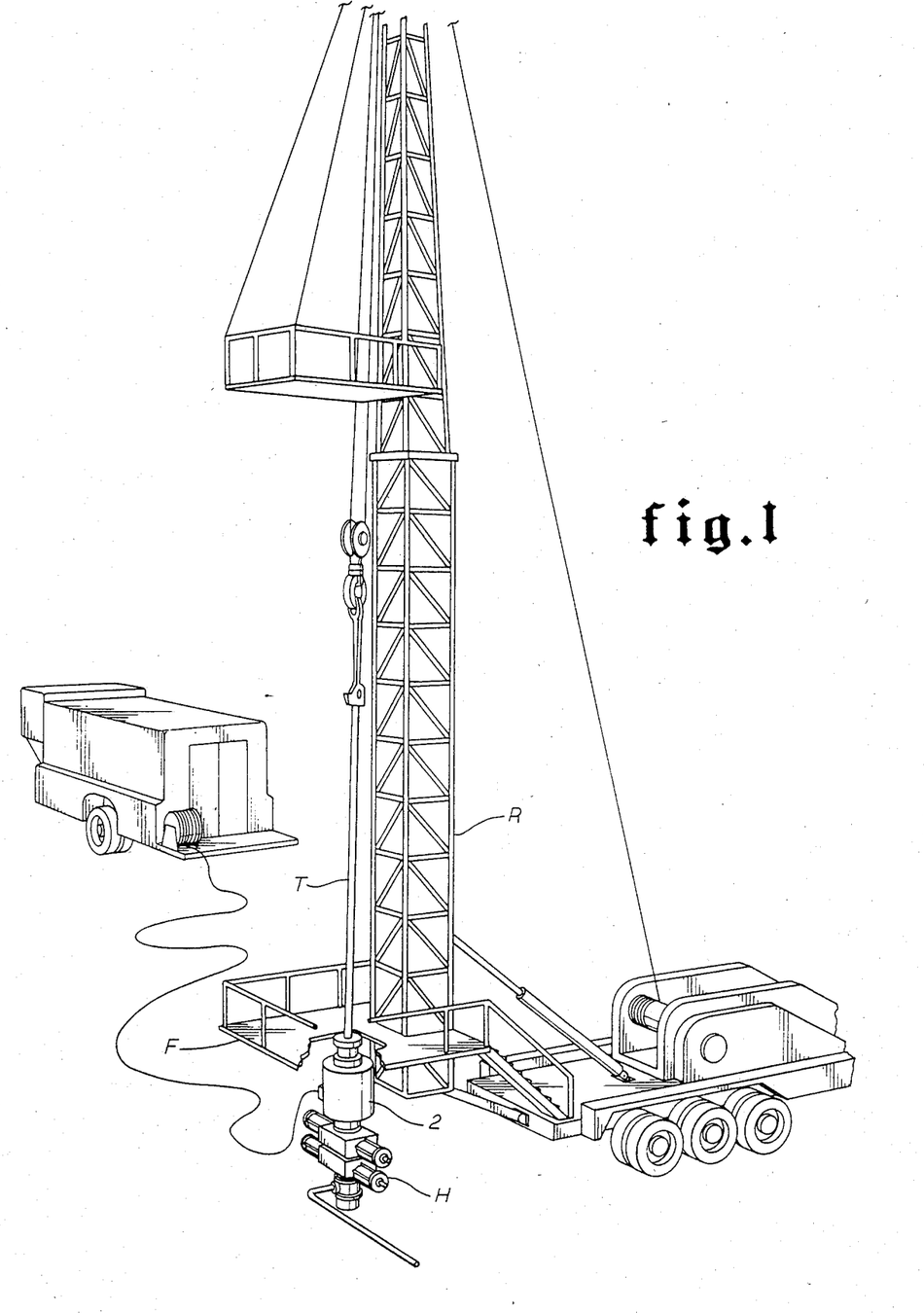
FIG. 1 is a schematic showing the tubing trip tool on a surface rig.

A conventional workover rig illustrated schematically by rig R in FIG. 1, is used to remove a tubular string, such as a casing, drilling or tubing string represented by tubing string T, from an oil or gas well during workover operations. Workover operations normally involve the removal of the tubular string to permit operations intended to restore or increase production in a producing well. Typically the original tubing string is reused if the respective tubular elements are in satisfactory condition. FIG. 1 illustrates the use of a tubing trip tool 2 at the rig site to measure defects in each tubular element as it is removed from the well. A tubing trip tool 2 comprising the preferred embodiment of this invention can be positioned on the wellhead H below the rig floor F so as not to interfere with conventional operations on the rig. The tubing trip tool can be attached directly to the blow out preventers on the well.

Figures 2, 3:
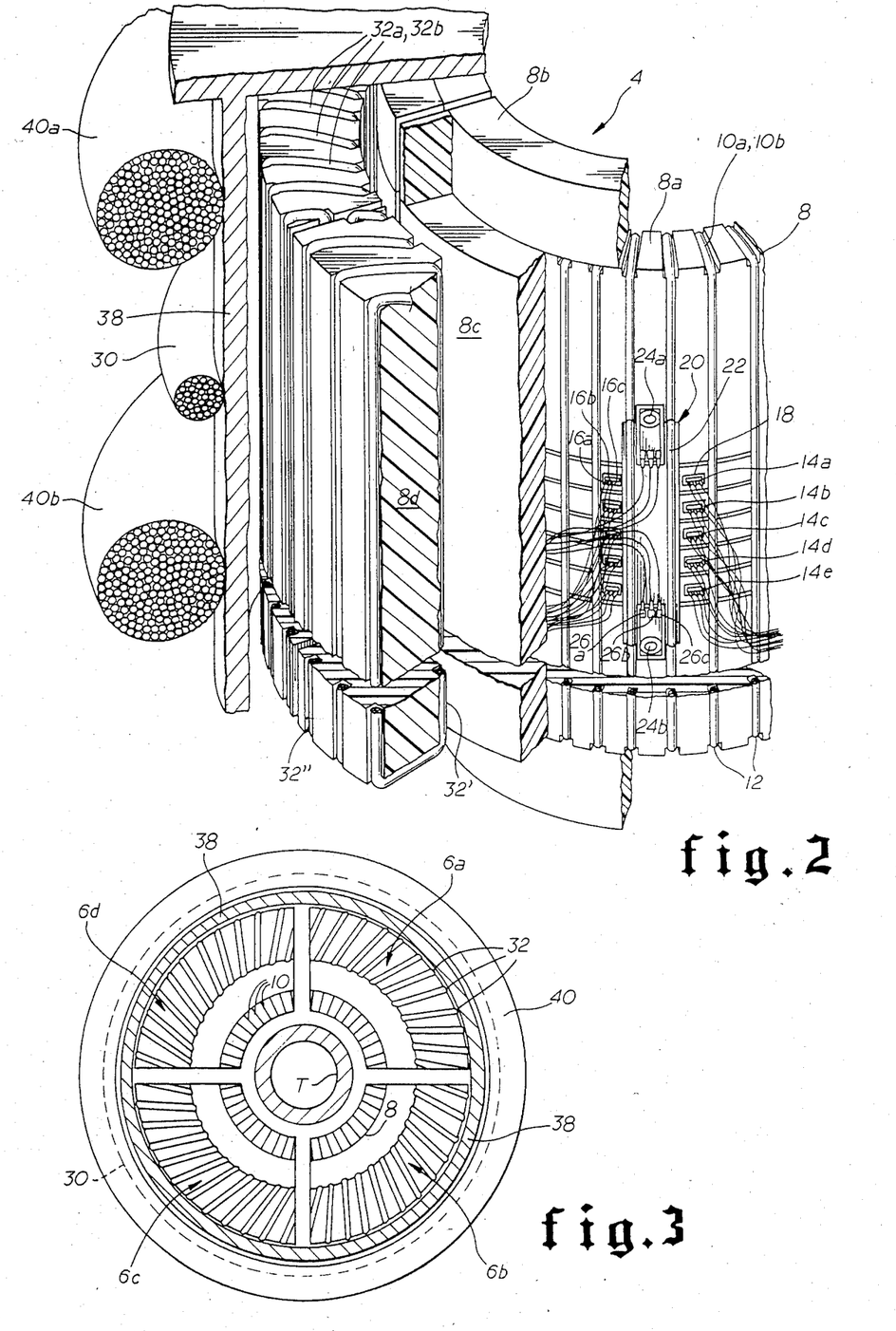
FIG. 2 is a view of a segment of the tubing trip tool in the expanded configuration.
FIG. 3 is a cross-sectional view of the tubing trip tool head in the expanded configuration.

A segment of the tubing trip tool head 4 is shown in FIG. 2. The head includes two separate driving coils, two separate detecting coils, and a plurality of discrete detecting elements to determine the extent of defects in the tubing sections. A velocity detector for determining relative velocity between the head and tubing sections is also included. The preferred embodiment of this invention comprises an expandable head having four segments 6a–6d as seen in FIG. 3. Each segment is an encasement 8 which comprises multiple components. The encasement 8 is fabricated from a material that has the properties of an electrical insulator. In the preferred embodiment of this invention, encasement 8 can be formed from an encapsulation material or potting compound which will insure that the proper amount of space is maintained between the electrical components. The encapsulation material will occupy any spaces or voids surrounding the components, and will provide a barrier between the electrical components and the atmosphere surrounding encasement 8, thereby rendering encasement 8 safe for use on the wellhead where explosive vapors can be encountered.

Two separate AC detecting coils 10a and 10b are carried on the innermost insulating body section 8a. The circumferentially continuous coils 10a and 10b are wound in appropriate grooves on body section 8a and a plurality of separate loops are formed around body 8a. These separate loops, each of which contains conductors forming the separate detecting coils 10a and 10b, are positioned in a radial plane on encapsulating member 8a. Each loop is generally defined by two radially spaced, axially extending coil conductor sections and two axially spaced, radially extending coil conductor sections. The coil conductors then define an annular volume encircling the tubular sections passing axially therethrough. Radially extending planes between the coil conductors will be generally perpendicular to magnetic field lines detected by coils 10a and 10b as will be subsequently more completely discussed.

A plurality of flux leakage detecting elements 14a–14e are also located in the inner encapsulating body section 8a. In the preferred embodiment of this invention, each of the flux leakage detecting probes 14a–14e comprises a separate probe in which voltage is generated in response to the Hall effect. The plane of each Hall probe is perpendicular to the axis of the tubing trip tool head 4 and is located perpendicular to each tubular element moving axially relative to the tubing trip tool head 4. In the preferred embodiment of this invention, separate groupings of five Hall effect flux leakage detecting probes are positioned at different angular positions around the tubing trip tool head 4. Each of the Hall probes 14a–14e is received within corresponding slots 18 extending into the insulating body section 8a. In the preferred embodiment of this invention, five equally spaced probes are positioned at each angular location.

One or more velocity detectors 20 is positioned on the exterior of insulating body section 8a. In the preferred embodiment of this invention, each velocity detector 20 comprises a detector circuit or coil 22 having two or more Hall probes 24a and 24b located within the circuit. The plane of the velocity detector circuit or coil 22 is perpendicular to a radial plane extending through the tubing trip tool head 8. The plane of the individual Hall probes 24a and 24b in the velocity detector is perpendicular to the plane of the Hall probe 14a–14e used for flux leakage detection.

The AC magnetic detecting coils 10a and 10b, the flux leakage detecting probes 14a–14e and the velocity detector 20 are each radially spaced from the tubing element T in which defects are to be measured. In the segmented embodiment of the invention shown in FIG. 2, the individual segments can be shifted radially from a measuring position to an outer position to permit obstructions to move past the tubing trip tool head. Each of the detector coils is, however, spaced from the surface of the tubing T in the inner measuring position. In the preferred embodiment of this invention, the inner surface of the tubing trip tool head 4 is positioned approximately two-thirds of an inch from the surface of the tubing element T.

Insulated body sections 8b and 8c surround the detecting coils and probes mounted on insulating body section 8a. Epoxy or some other potting material can also be used to insure that all potential electrical leakage paths are appropriately isolated from each other and from the atmosphere.

Outer AC driving coils 32a and 32b are positioned around insulating body section 8d. The AC drive coils 32a and 32b each comprise continuous coils having an angular conductor distribution similar to that of AC detecting coils 10a and 10b. The sinusoidal distribution in the coils 32a and 32b is relatively offset so that the conductor distribution phase differs between drive coils 32a and 32b. In the preferred embodiment of this invention, the conductor distribution is offset by 90° so that coil 32a can be referred to as a sine coil and coil 32b can be referred to as a cosine coil. Coils 32a and 32b each completely encircle the tubing trip tool head 4 and tubular element T with separate loops, containing conductors from each coil 32a and 32b, being formed in radial planes around the tubing trip tool head 4. On the exterior, AC driving coils 32 are encapsulated within the common encapsulating insulating body 8 of the tubing trip tool 2.

In the preferred embodiment of this invention, an outer metal sheath 38 can be positioned around the exterior tubing trip tool head. This outer metal sheath, which can be fabricated from a nonferromagnetic material, such as aluminum, serves as a carrier for the outer DC drive coils 40a and 40b and for encircling coil 30. In the preferred embodiment of this invention, the DC drive coils are separated into two separate bundles. A single drive coil bundle can also be used. The encircling drive coils 40 contain a sufficient number of amp turns to saturate the tubular element T passing through the tubing trip tool. Encircling coil 30 extends completely around the circumference of the tubing trip tool head 4 and surrounds the tubular element T at a greater radial spacing than the detecting elements 10a and 10b, 14a–14e, and 20.

WALL THICKNESS MEASUREMENT

The tubing trip tool 2 measures the wall thickness of a tubing section by using a technique in which the total flux induced in the tubing section by a saturating magnetic field is measured. The ferromagnetic tubing section within the saturating magnetic field is saturated when the magnitude of the magnetic field induced in the ferromagnetic element is at a maximum and does not increase as a result of a further increase in the saturating magnetizing field. Thus the saturating magnetizing field can produce a uniform saturated magnetic field in a tubing section having a specified cross-sectional area. In other words, the total magnetic flux is dependent upon the cross-sectional area or wall thickness of the tubular section. If the saturating magnetizing field is uniform, the contribution of the total flux induced by the magnetization of the pipe material within a given area varies as the cross-sectional area of the tubing section. By providing a large number of amp turns in a coil 40 encircling a tubing section, a saturated magnetic field extending longitudinally within the wall of the tubing section can be produced.

The total flux through an area intersecting the axis of the tubing section and intersecting the longitudinal saturated magnetic field can be measured by pickup coil 30 encircling the tubular section. The area of the pickup coil would preferably, but not necessarily, be perpendicular to the axis of the tubing section. The total flux through the pickup coil can be detected by signal integration. The EMF induced in a pickup coil is directly related to the time rate of change of the flux through the coil. Thus the total flux can be detected by integrating the EMF produced in the coil over time. In fact, a virtually linear dependence of the total flux through the pickup coil with average wall thickness can be obtained. Thus a convenient direct measurement of average wall thickness can be made.

LOCAL DEFECT DETECTION

Figure 4:
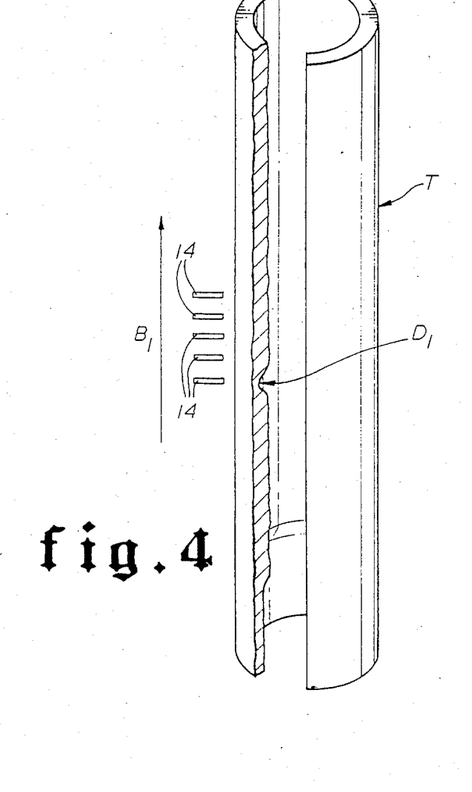
FIG. 4 is a view showing the tubing string and the detectors for measuring local defects.
Figure 5:
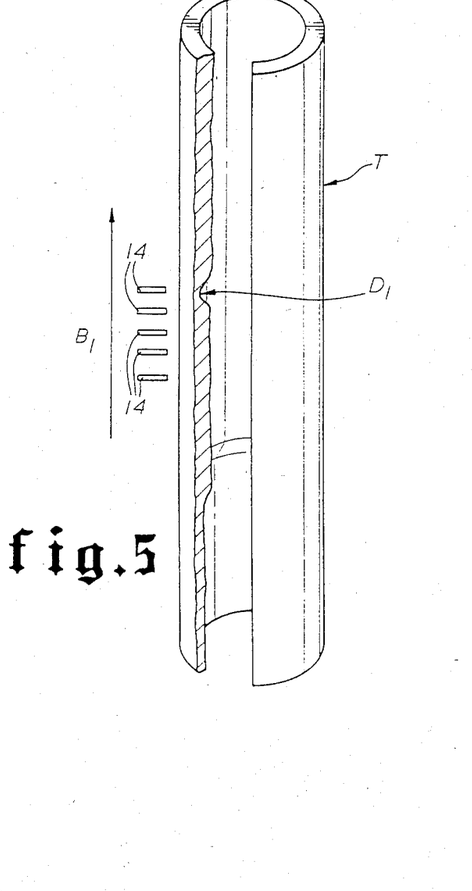
FIG. 5 is a view similar to FIG. 4 showing relative movement of the tubing.

The average wall thickness of a ferromagnetic tubular member or pipe can be determined by detecting the total flux induced by the saturating magnetizing field within the element. Qualitative information as to the changes in surface texture due to such factors as internal and external corrosion, can be determined by comparing average wall thickness at different locations of the tubular member. The difference between the signals produced in separate coils will not yield quantitative information as to the state of local defects in the tubular members. In tubular sections used in oil and gas wells, corrosion on the tubular member can result in localized corrosion pits $D_1$ which can seriously reduce the strength of individual tubing sections. Since the thickness of the remaining wall of the tubular sections determines the ability of individual tubular sections to function in the work environment, the depth of local corrosion pits must be quantified to determine the acceptability of the tubular sections.

It is common practice to grade used tubing based upon the depth of corrosion pits. Although each separate corrosion pit would constitute a local defect $D_1$, the dimensions of which would generally be less than the diameter of the tubular element, the nature of the corrosion phenomenon would result in a plurality of irregular and overlapping corrosion pits being located in the same general region on the interior of a tubular section. Of course the flux leakage will be dependent upon the overall size of individual corrosion pits and not just the depth of the corrosion pits. Thus the length and width of the corrosion pits would affect the flux leakage detected. Other factors, such as the contour or shape of the corrosion pits and the extent of any discontinuities in the shape of corrosion pits, would also affect the flux leakage. Thus the leakage fields of different pits having the same depth in a tubular section will differ for different lengths and widths of the pits as well as for a different contour of the pits. Background fields or noise due to unrelated phenomenon can also affect the signal corresponding to flux leakage and the saturated magnetic field within the pipe.

In the preferred embodiment of this invention, a plurality of flux leakage detecting elements 14 are disposed within the saturating magnetizing field. These flux leakage detecting elements are disposed at a plurality of axially spaced positions within the saturating magnetizing field. In the preferred embodiment of this invention, a plurality of discrete probes having an output produced by the Hall effect are used. In the preferred embodiment of this invention, identical flux leakage detecting Hall probes 14a-14e are equally spaced at five separate axial positions. Although only two sets of flux leakage detecting Hall probes 14a-14e are shown in FIG. 2, it should be understood that corresponding sets of multiple elements are circumferentially disposed around the tubing trip tool head to provide complete coverage around the periphery of the tubular element to detect local defects, such as corrosion pits located at different angular positions.

In the preferred embodiment of this invention, the individual flux leakage detecting Hall probes are oriented such that the plane of the Hall sensing element is perpendicular to the axis of the moving tubular element. Hall elements, such as the type used herein, produce an output voltage proportional to the product of the input current, the magnetic flux density, and the sine of the angle between the magnetic flux density and the plane of the Hall generator. Thus a maximum voltage output from a given leakage field would be produced by orienting the individual flux leakage detecting Hall probes perpendicular to the saturated magnetic field. The DC drive coils 40a and 40b are positioned to induce a longitudinal or axial saturated magnetic field within the tubular element T. By orienting the probes 14a-14e perpendicular to the longitudinal saturated magnetic field within the pipe, the flux leakage detecting probes are situated to detect longitudinal changes in the magnetic field. Of course transverse magnetic field changes would also occur as a result in the change in the longitudinal saturated field within the tubular member. Orientation of flux leakage detecting Hall probes perpendicular to the radius of a moving tubular section would be ideal to detect these transverse field changes. However, it is understood by those skilled in the art that the transverse magnetic field changes are related to longitudinal magnetic field changes. Thus a plurality of individual flux leakage detecting Hall probes oriented at right angles to the probes 14a-14e used in the preferred embodiment of this invention could also be used. Of course flux leakage detecting elements other than Hall probes can also be employed in the measurement of localized defects, such as the depth of corrosion pits. For example, the change in flux linking a coil will also result in a signal which can be employed for local defect measurement. However, the output signal from a coil must be integrated to obtain the same output independent of the velocity of tubing element T, as would be obtained with a Hall probe.

It has been found that the magnitude of the flux leakage detected by elements 14 does not provide an adequate quantitative measure of the depth of local defects, such as corrosion pitting defects, on a tubular element. The fact that flux leakage is dependent upon the size and shape of localized defects, such as corrosion pitting, rather than upon the depth alone, is believed to account for the inability to measure localized defect depth by measuring flux leakage magnitude alone. However, it has been found if effects due to the length and width of defects, such as corrosion pitting, can be removed, the resulting signal results in an accurate measurement of the depth of the local defect.

In the preferred embodiment of this invention, a signal corresponding to the depth of local defects, such as defects due to corrosion pitting, can be determined by differentiation of the magnitude of the flux leakage relative to the axial or longitudinal dimension of the moving tubular member.

AXIAL DEFECT MEARUREMENT

The bore of a tubular member or tubing section T used in a tubular string in a subterranean oil and gas well can often have axially extending defects $D_2$ located at one or more circumferential positions on the tubing. An example of axially extending defects are defects due to sucker rod wear. Sucker rod wear on the bore of the tubing occurs when the sucker rod contacts the tubing during reciprocal movement of the sucker rod. However, sucker rod interference is not uniform around the circumference of the bore of the tubing section or tubular element. Sucker rod wear often occurs at only one circumferential location, although it is not uncommon for a sucker rod to oscillate laterally causing sucker rod interference at two opposite points. The loads placed on the individual sucker rod assembly will normally result in continual interference between the sucker rod and the tubing at the same locations.

Since the length of the sucker rod stroke is normally large compared to the diameter of the tubing, the length of the sucker rod defects can be expected to be greater than the diameter of the tubing. Although sucker rod wear is a common occurrence, points at which the sucker rod interferes with the bore of a tubing string may occur in only a fraction of the tubing sections if the distance between interfering sucker rod nodes is greater than the length of individual tubing sections. Not only must the tubing sections subjected to sucker rod wear be identified, but the depth of axial defects, such as sucker rod wear defects, must also be measured. The depth of the defects due to sucker rod wear is significant because the reduction in the strength of the individual tubing section increases with the depth of the axially extending sucker rod wear defect.

Figure 6:
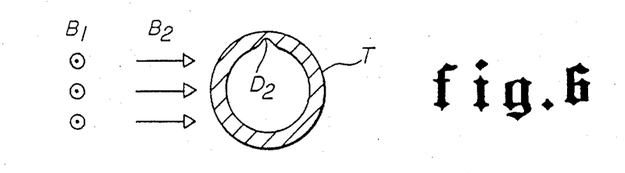
FIGS. 6–8 illustrate the rotation of the fluctuating magnetic field around a tubular element to detect axially extending defects at different angular positions relative to the driving magnetic field.
Figure 7:
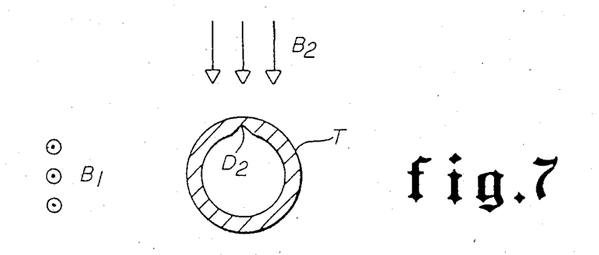
Figures 8, 9:
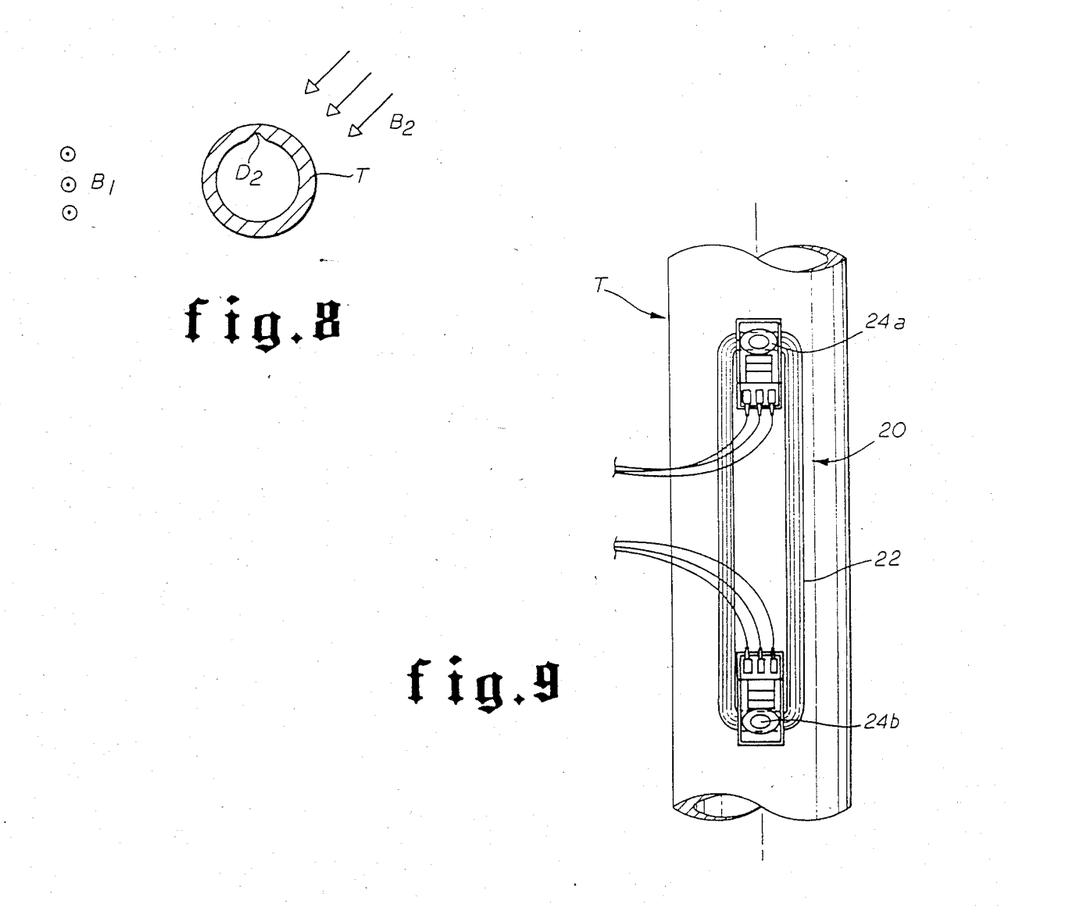
FIG. 9 is a view of a velocity detector mountable on the tubing trip tool head.

Axial defects $D_2$, such as defects due to sucker rod interference, can be detected by employing a fluctuating AC magnetizing field $B_2$ in addition to a uniform DC magnetizing field $B_1$. Even if a uniform DC magnetizing field in the longitudinal or axial direction is of sufficient intensity to saturate the ferromagnetic element or tubular section within the DC field, as is the case with the field used to determine wall thickness, the addition of a fluctuating AC transverse magnetic field will result in detectable changes in the magnetic state of the ferromagnetic element located within both fields. In fact, the DC field enhances the penetration of the AC field in the tubular sections. Of course the detectable changes resulting from the addition of the fluctuating transverse field will be dependent upon the geometry of the tubular element. For example, the response of an undamaged tubing section would differ from the response of a similar tubing section containing an axially extending defect, such as a rod wear interference defect. In the preferred embodiment of this invention, the changes due to such axially extending defects as sucker rod interference defects $D_2$ in an oil field tubular section can be detected even where the strength of the fluctuating transverse magnetic field is significantly less than the strength of a uniform saturating DC magnetizing field. It has been found that measurement of axial defects, such as sucker rod interference defects, can be made by applying a sinusoidal transverse magnetizing field having a frequency of approximately 100 Hz. and an intensity of approximately 1/10th the intensity of a uniform saturating magnetizing field applied in the longitudinal direction. In the preferred embodiment of this invention, drive coils 32 are used to apply such a fluctuating magnetizing field.

VELOCITY AND POSITION DETECTOR

The cross-sectional area of a moving tubular element, the depth of local defects, such as corrosion pitting defects, and the size of longitudinally extending defects, such as defects due to sucker rod interference, can be determined by detector 4 independent of the velocity of the tubular element T relative to the detector. There may also be a need to determine the velocity of the tubular element T relative to the tubing trip tool 2. For example, it may be necessary to not only determine the existence and size of a defect in a particular tubing section of tubular string T, but it may be necessary to determine the position of the defect in both the tubing string and in the constituent tubular section. A noncontact velocity detector 20 is shown positioned on the tubing trip tool head 4 in FIG. 2. The preferred embodiment of each velocity detector used in this invention comprises two detector elements 24a and 24b in which a signal is produced by the magnetic field. In the preferred embodiment of this invention, detector elements 24a and 24b comprise elements in which the voltage is generated due to the Hall effect. These Hall probes 24a and 24b are then incorporated into a velocity detector coil 22 as shown schematically in FIG. 9. The signal produced in the coil is related to both the velocity and the magnetic field sensed by the coil. The signal in the coil is proportional to the vector cross product of the velocity and the magnetic field whereas the signals in the Hall probes are due solely to the magnetic field. The output voltage of a pickup coil near a changing magnetic field is proportional to the rate of change of the field of fixed spatial orientation passing by the coil, then any output voltage is proportional to the product of the field strength and the field velocity.

The changing magnetic fields due to the velocity of the tubular element T are the magnetic leakage fields emanating from the pipe either as pitting signals, as signals due to average wall changes, or as pipe noise. For example, a leakage field is created by permeability fluctuations within the ferromagnetic tubular element T. In the preferred embodiment of each velocity detector, the two Hall probes 24a and 24b are incorporated into the coil 22 with the Hall probes oriented to detect radial changes in the leakage fields. When the coil and Hall probes are oriented as shown in FIG. 2, the coil voltage is equal to the product of the number of turns in the coil, the velocity of the tubular element, the width of the coil, and the difference between the radial components of the magnetic leakage field at the two ends of the coil. The voltage of each Hall probe is equal to the gain of the Hall probe device times the radial component of the leakage field of the Hall probe. The ratio of the coil voltage to the difference in the voltage between the two Hall probes thus determines the pipe velocity.

Figure 10:
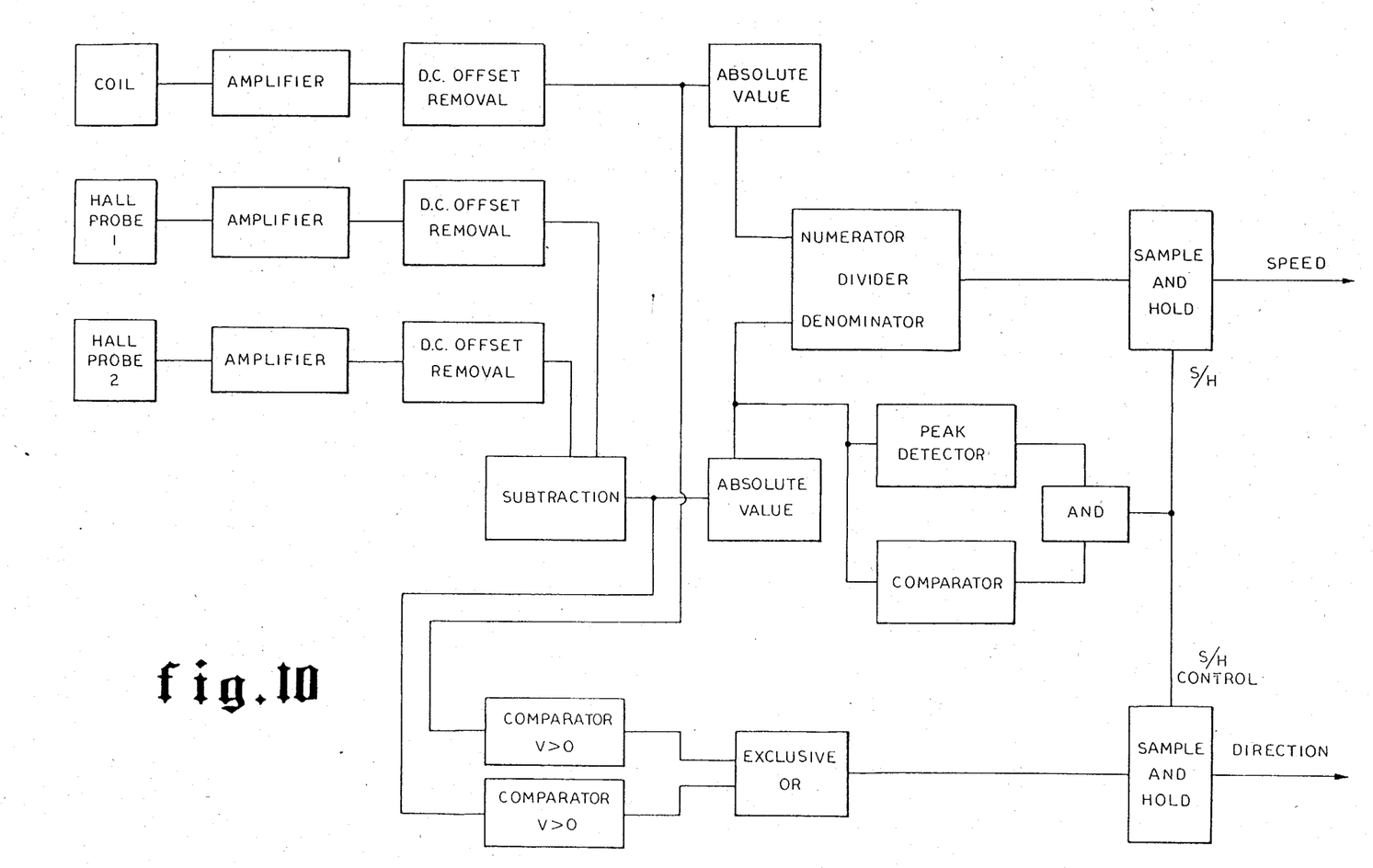
FIG. 10 is a diagram of the signal processing for the velocity detector.

A block diagram of analog electronics which could be used to measure the velocity of a tubular element is shown in FIG. 10. The absolute values of the signals must be used in accomodate the divider. A sample and hold detector is used to eliminate the erroneous measurements that occur when the denominator is small or rapidly changing. It is operated such that the velocity is updated only when the Hall probe difference is at a peak and within a reasonable voltage range. The direction of motion is determined by correlating the polarity of the coil signal and the Hall probe difference. It will be understood, of course, that other conventional circuits could be used to determine the velocity measurement.

The velocity detector employed in the tubing trip tool head 4 is located on the exterior of the detector coils 10. The velocity detector can be spaced from the surface of the ferromagnetic tubular element T and need not be in contact with the tubular element. In the preferred embodiment of this invention, the velocity detector can be transversely positioned approximately 0.650 inches from the surfaces of the tubular element. The detector is insensitive to radial position, applied field, signal amplitude and pipe grade. This noncontact velocity measurement is especially useful in conjunction with removal or insertion of the tubing string T from an oil or gas well. In the preferred embodiment of this invention, this velocity measurement permits the operator to determine the axial position along the tubular element and along each individual tubing section.

END COUPLING DETECTOR

The noncontact velocity detector described herein can be used to determine the axial position of a defect in an inspected tubular member. Knowledge of the defect location in specific tubular sections forming the tubing string is important, and knowledge of the defect location in the tubing string is also significant in that such knowledge would permit the operator to determine the exact location in the well at which wall thickness reduction, corrosion pitting or wear due to sucker rod interference is a problem. Such knowledge would permit construction of a string profile to determine significant problem areas.

In order to construct a string profile and to accurately obtain information as to the location of defects in any particular tubular string, the position of the tubing string relative to the well head must be determined. In the preferred embodiment of this invention, the location of the tubing string is determined by use of the noncontact velocity detector and by use of a noncontact end coupling detector. For conventional tubular strings, such as casing production tubing and completion strings used in oil and gas wells, the individual sections are joined by end couplings.

There are two common types of end couplings. The first consists of a collar having internal threads on both ends which is used to join two lengths of casing, tubing or conduit. The cross-sectional area of the separate coupling member and the end portions of the tubing sections engaging the separate member will be greater than the cross-sectional area of the tubular section intermediate its ends. A second type of end coupling comprises an upset section on the ends of adjacent tubing sections. The ends of adjacent tubing sections have mating threads in the vicinity of the upset ends, and the tubular sections are joined directly without the necessity of employing a separate coupling section or collar. These directly engageable tubular sections are, however, upset, with the portion of the tubing section in which threads are machined being thicker than the remaining portion of the tubing section. Thus the cross-sectional area in the vicinity of the end coupling is greater than the cross-sectional area of the tubing intermediate its ends whether a separate collar is used or whether interengageable mating threads are employed on adjacent tubular sections.

Figure 11:
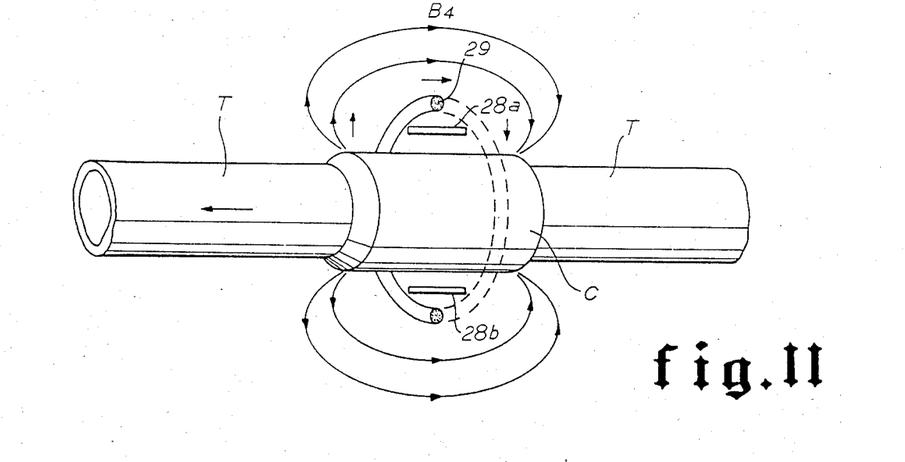
FIG. 11 is a view of the end coupling detector.

The exact location of each tubing section, and thus the location within the tubular string can be determined by detecting both the presence and the direction of movement of each end coupling. In the preferred embodiment of this invention, a magnetic field having a uniform strength and fixed relative to the well head is applied to the portion of the tubular string and tubular sections in the vicinity of the well head. An induced magnetic field in the tubular section results. FIG. 11 shows tubing sections T interconnected by end coupling C and the lines of magnetic flux representing the induced magnetic field B4 in the area of end coupling C. Since the cross-sectional area at end coupling C is greater than the cross-sectional area of tubing T, the strength of the magnetic field B4 in the vicinity of the end coupling will be greater than the strength of the magnetic field induced in the tubular section intermediate its ends. If the strength of the magnetic field B4 detected at the well head is greater than a predetermined reference value in excess of the field strength normally induced in a tubing section having a constant cross-sectional area intermediate its ends, the presence of a coupling can be distinguished from normal variations in the strength of the induced magnetic field in the tubing section. In the preferred embodiment of this invention, the strength of the reference signal or the threshold value of the magnitude of the induced magnetic field would be less than the magnitude of a magnetic field normally induced by an end coupling of known dimensions to account for slight variations of the magnetic field induced in the coupling.

In normal drilling, production and completion operations, the tubular sections comprising the tubular string are intermittently lowered and raised during either insertion or removal into or from the well. Therefore simple detection of the presence of an end coupling in the vicinity of the well head will not be sufficient to identify specific tubular sections comprising the tubular string or to identify the location of a tubular section within the tubular string. Therefore it will be necessary to identify the direction in which the coupling moves with relation to the well head. By identifying both the presence of the coupling at the well head and the direction of movement of the coupling with respect to the well head, each instance in which the coupling passes the well head in either direction can be stored in a conventional memory, and conventional computing means can be provided to tabulate the number and location of each end coupling encountered during insertion or removal of the tubular string into or from the well.

In the preferred embodiment of this invention, each end coupling, and its direction of movement are detected and counted by first magnetically detecting the presence of an end coupling having an enlarged cross-sectional area in the manner previously described. One or more detectors capable of generating signals of opposite signs corresponding to movement of the tubular strings T and end coupling C in opposite directions relative to the detector are employed to determine the direction of movement of an end coupling C. In the preferred embodiment of this invention, an encircling coil 29 similar to encircling pickup coil 30, which is used to determine the average wall thickness of the tubular section, is employed to detect an end coupling C having a greater thickness than the tubular section. Encircling coil 29 functions in the same manner as coil 30 as previously described with respect to measurement of the wall thickness. Indeed an apparatus in accordance with this invention could employ the same encircling coil, both for the wall thickness measurement of the tubular string T and to detect the presence of an enlarged end coupling C.

Once the presence of the end coupling has been detected by encircling coil 29, the direction of movement can be detected by separate detectors, such as detectors 28a and 28b. In the preferred embodiment of this invention, detectors 28a and 28b comprise Hall probes which generate a voltage proportional to the product of the input current, the magnetic flux density, and the sine of the angle between the magnetic flux density and the plane of the Hall generator. These elements are similar to the elements used for corrosion pitting detection and the voltage is produced in response to the electromagnetic phenomenon generally referred to as the Hall effect. The sign of the output voltage of Hall probes 28a and 28b will be opposite when subjected to magnetic lines of force in a magnetic field extending in opposite directions. As shown in FIG. 11, in which the direction of movement of the tubular string T is in the direction of the arrow, the magnetic lines of force of magnetic field B4 extend in the directions shown. Magnetic lines of force for the end coupling C increase in intensity as the end coupling C moves into an applied magnetic field when the magnetic lines of force extend outward as shown. At the trailing edge of the end coupling C, the magnetic lines of force in the induced magnetic field B4 extend inwardly toward the tubular string T and end coupling C as shown schematically in FIG. 11. Thus the Hall probes 28a and 28b will be subjected to magnetic lines of force or flux extending in opposite directions during passage of end coupling C through the applied magnetic field. When the Hall probes 28a and 28b are positioned near the leading edge of the moving end coupling C, the magnetic lines of force will extend radially outward. When the Hall probes 28a and 28b are adjacent the trailing edge of the end coupling C, they will be subjected to magnetic line of forces extending inwardly toward end coupling C. Thus the voltage generated by Hall probes 28a in the vicinity of the leading edge of end coupling C will have the opposite sign from the voltage generated when the Hall probes 28a and 28b are in the vicinity of the trailing edge of end coupling C. One sequence of the signs of the voltage generated by Hall probes 28a and 28b will correspond to movement of the tubing string T and end coupling C in the direction shown in FIG. 11. Movement of the tubing string T and the end coupling C in the opposite direction will result in an opposite sequence for the signs of the voltage generated by the Hall probes 28a and 28b. Thus the direction of movement of end coupling C through the applied magnetic field can be recognized by conventional computing means and specific tubular sections can be located.

When used in conjunction with a position indicator, such as would be provided by a device capable of measuring the velocity of the tubing string T, a profile of defects, including average wall thickness reduction, corrosion pitting, and wear due to sucker rod interference, can be tabulated as a function of the position of the tubular string in the well. Such information can give the operator valuable insights on the phenomenon being encountered within a subterranean oil or gas well. Furthermore, the use of the end coupling detector and the velocity detector described in the preferred embodiment of this invention will permit an accurate tabulation of defects in individual used tubing sections, to permit the operator to determine if such tubing sections should be replaced.

Although the invention has been described in terms of the specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A method of measuring the axial velocity of a relatively moving ferromagnetic element, comprising:
   applying a uniform magnetic field to a portion of the element;
   detecting a first signal dependent upon the axial velocity of the tubular element relative to the uniform magnetic field and upon the magnetic leakage fields emanating from the element as a result of axial changes in the magnetic properties of the element;
   detecting a second signal dependent only upon the changing magnetic leakage fields emanating from the element as a result of axial changes in the magnetic properties of the element; and
   comparing the first and second signals to measure the axial velocity of the tubular element.

2. The method of claim 1 comprising the further step of measuring the axial velocity of the element by detecting, at a fixed location within the uniform magnetic field, a signal induced in a circuit by movement of the element relative to the uniform magnetic field and comparing the last mentioned signal in the circuit to a signal simultaneously induced by the magnetic flux density of the magnetic flux leakage field.

3. The method of claim 2 wherein the axial velocity is detected by comparing the voltage induced around a circuit comprising a plurality of circuit elements, in which the voltage across each circuit element is proportional to the magnetic flux leakage density of the flux leakage magnetic field, with the difference between the voltage in circuit elements due to relative mutual displacement within the saturating magnetic field.

4. The method of claim 2 wherein the voltage across each of the plurality of circuit elements is generated by the Hall effect.

5. A method of measuring the axial velocity of tubing sections, comprising a continuous tubing string used in a subterranean well bore, at the well head as the tubing string travels into and out of the well bore, comprising the steps of:
   applying a uniform magnetic field to the tubing sections at the well head as the tubing string is moved into or out of the well bore;
   detecting a first signal dependent upon the axial velocity of each tubing section relative to the well head and upon the changing magnetic leakage fields emanating from each tubing section as a result of axial changes in the magnetic properties of each tubing section;
   detecting a second signal dependent only upon the changing magnetic leakage fields emanating from each tubing section as a result of axial changes in the magnetic properties of each tubing section; and
   comparing the first and second signals to measure the axial velocity of each tubular section relative to the well head.

6. In a method of measuring and locating defects in a tubular element during axial movement, the steps of magnetically saturating a portion of the tubular element to measure the thickness thereof; detecting magnetic flux leakage changes to measure localized defects; applying an additional magnetic field to detect longitudinal defects in the element, the improvement comprising the steps of:
   measuring the axial velocity of the element by detecting a first signal dependent upon the axial velocity of the element and upon a moving magnetic field which is variable due to actual displacement of the element and comparing the first signal to a second signal dependent upon the moving magnetic field alone;
   processing said axial velocity to locate said defects.

7. In the method of claim 6 wherein the moving magnetic field is a magnetic leakage field.

8. In the method of claim 6 wherein the step of measuring the axial velocity of the tubular element comprises the detection, at a fixed location within a magnetic field, of a signal induced in a circuit by axial movement of the element relative to the last mentioned magnetic field and comparing the last mentioned signal in the circuit to a signal simultaneously induced by the magnetic flux density of the last mentioned magnetic field.

9. In the method of claim 8 wherein the last mentioned magnetic field is the magnetic flux leakage of a saturated magnetic field.

10. In the method of claim 9 wherein the axial velocity is detected by comparing the voltage induced around a circuit comprising a plurality of circuit elements, in which the voltage across each circuit element is proportional to the magnetic flux leakage density of the saturated magnetic field, with the difference between the voltage in circuit elements due to relative mutual displacement within the saturating magnetic field.

11. In the method of claim 10 wherein the voltage across each of the plurality of circuit elements is generated by the Hall effect.

12. In the method of claim 6 wherein the processing of the axial velocity comprises the further step of determining the axial location of measured defects by detecting the ends of each tubular section and determining the axial location by integrating the magnetic axial velocity measurement.

13. A tool for measuring the axial velocity of a tubular element comprising:
   means transversely spaced from the tubular element for successively applying a uniform magnetic field during axial movement of the tubular element;
   means for detecting a first signal dependent upon the axial velocity of the tubular element relative to the uniform magnetic field and upon the changing magnetic leakage fields emanating from the tubular element as a result of axial changes in the magnetic properties of the tubular element;

means for detecting a second signal dependent only upon the changing magnetic leakage fields emanating from the tubular element as a result of axial changes in the magnetic properties of the tubular element; and means for comparing the first and second signals to measure the axial velocity of the tubular element.

14. The tool of claim 13 wherein the means for detecting the first signal comprises means for detecting the changing magnetic flux, of the magnetic field induced in the tubular element, linking a circuit transversely spaced from the tubular element due to axial movement thereof.

15. The tool of claim 14 wherein the means for detecting the second signal comprises at least two separate elements within the circuit.

16. The tool of claim 15 wherein the separate elements in the circuit comprise elements generating a voltage due to the Hall effect.

17. The tool of claim 13 wherein the means for applying a saturating magnetic field comprises electric coil means encircling the tubular element.

18. A tubing trip tool for measuring the axial velocity of tubing sections, comprising a continuous tubing string used in a subterranean well bore, at the well head as the tubing string travels into and out of the well bore, comprising:

means transversely spaced from the tubing sections at the well head for successively applying a uniform magnetic field during axial movement thereof relative to the well head;

means for detecting a first signal dependent upon the axial velocity of the tubing section relative to the uniform magnetic field and upon the changing magnetic leakage fields emanating from the tubing section as a result of axial changes in the magnetic properties of the tubing section;

means for detecting a second signal dependent only upon the changing magnetic leakage fields emanating from each tubing section as a result of axial changes in the magnetic properties of the tubing section; and means for comparing the first and second signals to measure the axial velocity of the tubing section.

19. The tool of claim 18 wherein the means for detecting the first signal comprises means for detecting the changing magnetic flux, of the magnetic field induced in each tubing section, linking a circuit transversely spaced from the tubing section due to axial movement thereof.

20. The tool of claim 19 wherein the means for detecting the second signal comprises at least two separate elements within the circuit.

21. The tool of claim 20 wherein the separate elements in the circuit comprise elements generating a voltage due to the Hall effect.

22. The tool of claim 18 wherein the means for applying a uniform magnetic field comprises electric coil means encircling the tubing section.

* * * * *